(12) United States Patent
Park (10) Patent No.: US 11,141,304 B1
(45) Date of Patent: Oct. 12, 2021

(54) DEVICE FOR ASSISTING HUMAN BODY BENDING/STRETCHING USING ELASTIC BODY

(71) Applicant: Donggwan Park, Busan (KR)

(72) Inventor: Donggwan Park, Busan (KR)

( * ) Notice: Subject to any disclaimer, the term of this patent is extended or adjusted under 35 U.S.C. 154(b) by 448 days.

(21) Appl. No.: 16/336,444

(22) PCT Filed: Nov. 23, 2017

(86) PCT No.: PCT/KR2017/013403
§ 371 (c)(1),
(2) Date: Mar. 25, 2019

(87) PCT Pub. No.: WO2018/097613
PCT Pub. Date: May 31, 2018

(30) Foreign Application Priority Data

Nov. 28, 2016 (KR) .......................... 10-2016-0158927
Sep. 25, 2017 (KR) .......................... 10-2017-0123083

(51) Int. Cl.
*A61F 5/02* (2006.01)
*A61F 5/01* (2006.01)

(52) U.S. Cl.
CPC ...... *A61F 5/028* (2013.01); *A61F 2005/0197* (2013.01)

(58) Field of Classification Search
CPC .......... A61F 2/44; A61F 2/446; A61F 2/4465; A61F 5/024; A61F 5/026; A61F 5/028; A61F 2002/3631; A61F 2/40; A61F 2/00; A61F 2/4612; A61F 2/581; A61F 2007/003; A61F 2007/0024; A61F 2007/0025; A61F 2007/0026; A61F 2007/0027; A61F 2005/0197
See application file for complete search history.

(56) References Cited

U.S. PATENT DOCUMENTS

| 2,828,737 | A | 4/1958 | Hale |
| 5,876,361 | A | 3/1999 | Harris |
| 7,549,968 | B2 * | 6/2009 | Cojbasic ................. A61F 5/026 128/874 |
| 2008/0161738 | A1 * | 7/2008 | Giesen .................... A61F 5/026 602/19 |
| 2010/0268137 | A1 | 10/2010 | Bachmann et al. |
| 2013/0110021 | A1 | 5/2013 | Liu et al. |

(Continued)

FOREIGN PATENT DOCUMENTS

CN 103919598 7/2014
EP 2070495 A1 6/2009
(Continued)

OTHER PUBLICATIONS

Search Report dated May 29, 2020 for European Application No. 17874453.8.

(Continued)

*Primary Examiner* — Tarla R Patel (57) ABSTRACT

The present invention relates to a bending/stretching capability improving device worn on a human body, which reduces a load on the waist in an equivalent amount to the combination of an acting repulsive force from an elastic body and an action of a tension winch during a bending/stretching exercise or when a weight is lifted, and which accordingly reduces damage to the waist.

6 Claims, 6 Drawing Sheets

(56) References Cited

U.S. PATENT DOCUMENTS

| | | |
|---|---|---|
| 2013/0281901 A1 | 10/2013 | Ochoa |
| 2014/0200615 A1 | 7/2014 | Yeh |
| 2015/0141892 A1 | 5/2015 | Ingimundarson et al. |

FOREIGN PATENT DOCUMENTS

| | | |
|---|---|---|
| JP | 2004358196 A | 12/2004 |
| JP | 2008067762 | 3/2008 |
| JP | 2011251001 A | 12/2011 |
| JP | 2012024557 A | 2/2012 |
| JP | 2013132396 A | 7/2013 |
| JP | 2016067774 | 5/2016 |
| KR | 101074235 | 10/2011 |
| KR | 101641883 | 7/2016 |
| WO | WO2015157731 A1 | 10/2015 |
| WO | WO2015166224 A1 | 11/2015 |
| WO | WO2016140363 A1 | 9/2016 |
| WO | WO2016190598 | 12/2016 |

OTHER PUBLICATIONS

Search Report dated Mar. 29, 2018 for PCT Application No. PCT/KR2017/013403.

\* cited by examiner

DEVICE FOR ASSISTING HUMAN BODY BENDING/STRETCHING USING ELASTIC BODY

CROSS-REFERENCE TO RELATED APPLICATIONS

This application is a U.S. National Phase of International Application No. PCT/KR2017/013403, filed Nov. 23, 2017, which claims priority to Korean Patent Application Nos. 10-2016-0158927, filed Nov. 28, 2016 and 10-2017-0123083, filed Sep. 25, 2017.

TECHNICAL FIELD

The present invention relates to a device for assisting bending and stretching of a human body with an elastic body is worn on an upper part of the human body, the device which is maintained in the intact state when the human body is standing upright, and which stores gravity energy changing according to a position of the upper body part upon bending of the human body in the elastic body and an electronic device and reuses the stored energy, so that consumption of human energy and a load on the back and the waist of the human body are reduced and thus bending is enabled even with a small amount of force and intensity of pressing the waist is increased in proportion of an angle of the bending, thereby reducing displacement of lumbar: that is, the device which is to be worn on a worker working in a manufacturing industry or a patient in need of waist reinforcement for a medical purpose to improve bending and stretching capability of a human body.

BACKGROUND ART

When a worker works in a manufacturing industry or an agricultural industry with bending his or her body and lifts a heavy object, load of one direction is applied to the waist and the back in proportional to an angle of the bending, in addition to the weight of the upper body part itself and the weight of the object, and this leads to fatigue or damage to the back: however, there is no solution for solving this problem easily.

Conventionally, abdominal binders, bands, belts, etc. are used to protect the waist for a medical purpose, and wearable robots are used these days, but the conventional protectors and the like fails to reduce load applied to an upper part of a human body and rather hampers flexibility of a body motion and the wearable robots depend on external power and are not economic-efficient for general use.

DISCLOSURE

Technical Problem

One object of the present invention is to reduce load applied to the waist and the back upon bending and stretching of a human body, which are not capable of being addressed with a conventional waist protector, belt, and the like, while helping the human body to be maintained flexible, thereby reducing fatigue from a body exercise in the same amount for the same time period and preventing displacement and departing of lumbar so as to protect the waist.

Another object of the present invention is to manufacture a device like a wearable robot for improving economic efficiency and use convenience by reusing energy of a human body for bending and stretching and by adding external power.

Technical Solution

The present invention is to provide a device for assisting bending and stretching of a human body using an elastic body, the device which is characterized in that a force generated due to displacement of an upper body part upon bending of the upper body part (the force of gravity, positional energy) is stored in the elastic body and an electronic device and the stored energy is recycled when the upper body part returns to an upright state, thereby reducing energy consumption of the human body.

The device includes: an integrated plate coil elastic body in which a plate spring is shaped in a coil to have a bending, tensing, rotating repulsive force or a complex elastic body designed to adjust a total bending repulsive force by combining a bending repulsive force of the plate spring and a tensing force of an additional coil spring; an upper fixing belt worn on an upper body part; and a lower belt worn on a lower body part (pelvic region), wherein the lower fixing bell fixes a lower side of the elastic body vertically and the upper fixing belt pulls an upper side of the elastic body so that a repulsive force occurs on the elastic body. In addition, the elastic body forms a coil-shaped frame or a plurality of blocks, which conform to curvature of a back of the human body (shape of spine), and variable points brought into contact with the back of the human body upon bending of the human body act as variable supports for the elastic body, causing a repulsive force to occur.

In addition, it is characterized in that tension of a tension wire of the integrated plate coil elastic body or tension of a coil spring of the complex elastic body is adjustable, so that additional power is added for a bending motion.

In addition, it is characterized in that an electric motor of a tension winch for tension adjustment is converted into a generator when a winch is released upon bending of the human body, and generated electricity goes back to an external power source, thereby minimizing consumption of external power.

Advantageous Effects

As a predetermined amount of change in positional energy resulted from bending and stretching of a human body is stored in an elastic body and recycled, energy consumption of the human body may be reduced, thereby making it easy to bend and stretch the body and reducing fatigue from the bending and stretching.

In addition, as load repeatedly concentrated and applied to a waist (lumbar) is reduced, one-directional motion is enabled for a longer period of time, and pressed lumbar is prevented from being pushed backward upon bending, thereby protecting the waist.

In addition, when a user lifts a heavy object while working, load on the user's waist may be reduced as much as a repulsive force of the elastic body and acting of the tension winch.

BEST MODE FOR INVENTION

Figure 1:
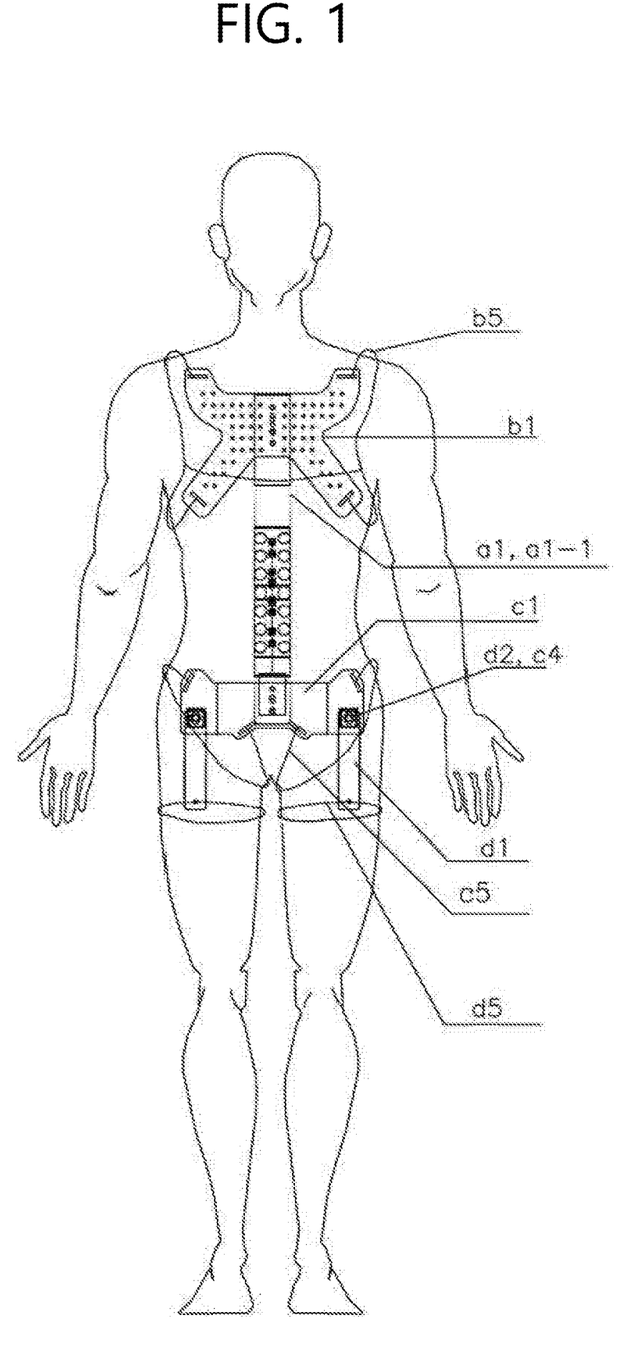
FIG. 1 shows a state in which a device for assisting bending and stretching of a human body according to the present invention is worn, and components of the device.

In FIG. 1,

A human body bending/stretching assistant device, in which upper/lower wearing belts and an elastic body are integrated so as to be worn on like a clothing, and which is shaped such that a surface to be brought into contact with a human body conforms to the curvature of the human body so as to match bending/stretching of the human body and bending/stretching of the elastic body to increase usability of a repulsive force of the elastic body, and, when the human body and the elastic body bends, the device generates electricity as a electric motor controlled by a motion of the human body and stores the electricity in an external power source and applies external power to the electric motor upon stretching of the human body and the elastic body, thereby increasing a total bending and stretching capability which is combinations of a bending and stretching capability of the human body with a repulsive force of the elastic body, an external force.

Mode for Invention

In FIG. 1,

The device of the present invention is depicted as being worn on by a human body, an upper frame b1 is fixed to an upper body part through an upper wearing belt b5, and a lower frame c1 is fixed to a lower body part through a lower wearing belt c5. A plate coil elastic body a1 or a complex electric body a1-1 is vertically connected to the upper and the lower frames b1 and c1. An extension frame d1 is coupled to the lower frame c1 through a connection plug d2 and an extension frame connection socket c4, and fixed to a human thigh with an extension frame belt d5.

Figure 2:
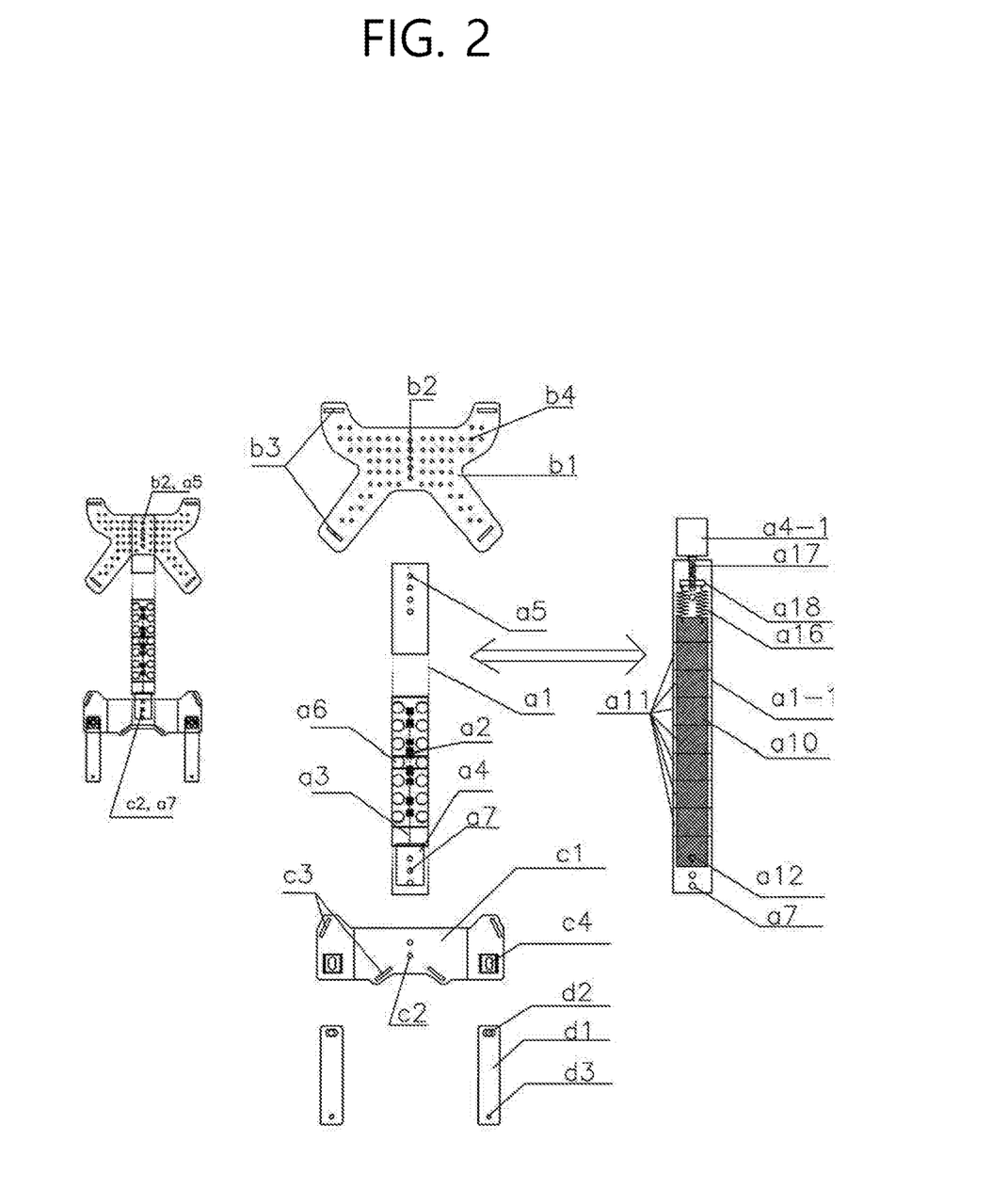
FIG. 2 is a detailed view showing an elastic body, upper and lower frames and wearing belts, a lower extension frame, and a wearing belt, wherein each component is indicated by a reference numeral.

In FIG. 2,

The upper frame b1 is of a high elasticity material and maintains a cross-sectional distance between four spots connected to the upper wearing belt b5 through upper wearing belt fixing holes b3 and one spot connected to the elastic body upper frame coupling hole a5 through elastic body upper coupling holes b2, and, when the cross-sectional distance is about to increase due to acting of the plate coil elastic body a1 or the complex elastic body a1-1 (when the upper body part bends), a repulsive force against the horizontal bending occurs to assist the acting of the plate coil elastic body a1 or the complex elastic body a1-1. As the plurality of elastic body upper coupling holes b2 is provided in the upper frame b1, the upper frame b1 may be adjusted to a height of a user, and, as a plurality of upper frame dissipation holes b4 is provided, inconvenience caused by heat dissipated when the user moves may be reduced.

The plate coil elastic body a1 is one-body plate spring that is formed in a coil spring which is shaped to conform curvature of the upper body part, and an absolute length of the plate is longer than the upper body part due to the coil. Accordingly, a bending repulsive force of a relatively thick and strong plate spring may be reduced and, at the same time, the strong plate corresponds to tensioning and twisting caused by a body motion. A plurality of acupressure protrusions a6 is attached to a surface of the plate coil elastic body a1, which is to come into contact with the waist, a plurality of tension pulley a2 is installed inside the coil shape, and a tension wire a3 is connected through the tension pulleys a2 to a tension winch a4 installed at a lower side of the plate coil elastic body a1.

The complex elastic body a1-1 is interchangeable with the plate coil elastic body a1, and a plurality of blocks a11 is connected to one another with ball joints or hinges a13. A plate spring a10, a coil spring a16, a tension adjustment screw a17, and a tension adjustment motor a7-1 form one axis in the inside of blocks on the opposite of the connection hinges.

The lower frame c1 is of a high elasticity material, and maintains a minimum cross-sectional distance between four spots connecting to a lower wearing belt c5 through lower wearing belt fixing holes c3 and one spot connected to the elastic body lower frame coupling hole a7 through the elastic body lower coupling hole c2, and, when a cross-sectional distance is about to increase due to acting of the plate coil elastic body a1 or the complex elastic body a1-1 (when the upper body part bends), a horizontal bending repulsive force occurs to assist the acting of the plate coil elastic body a1 or the complex elastic body a1-1. At the same time, the lower frame c1 vertically maintains and fixes the elastic body a1 or a1-1 so as to assist a bending repulsive force of the elastic body a1 or a1-1 more effectively.

The extension frame d1 is used when it is not possible to respond to a great repulsive force applied to the plate coil elastic body a1 with clamping forces of the lower frame c1 and the lower wearing belt c5, and the extension frame d1 reinforces a force of vertically maintaining the bottom of the plate coil elastic body a1 of the lower frame c1.

Figure 3:
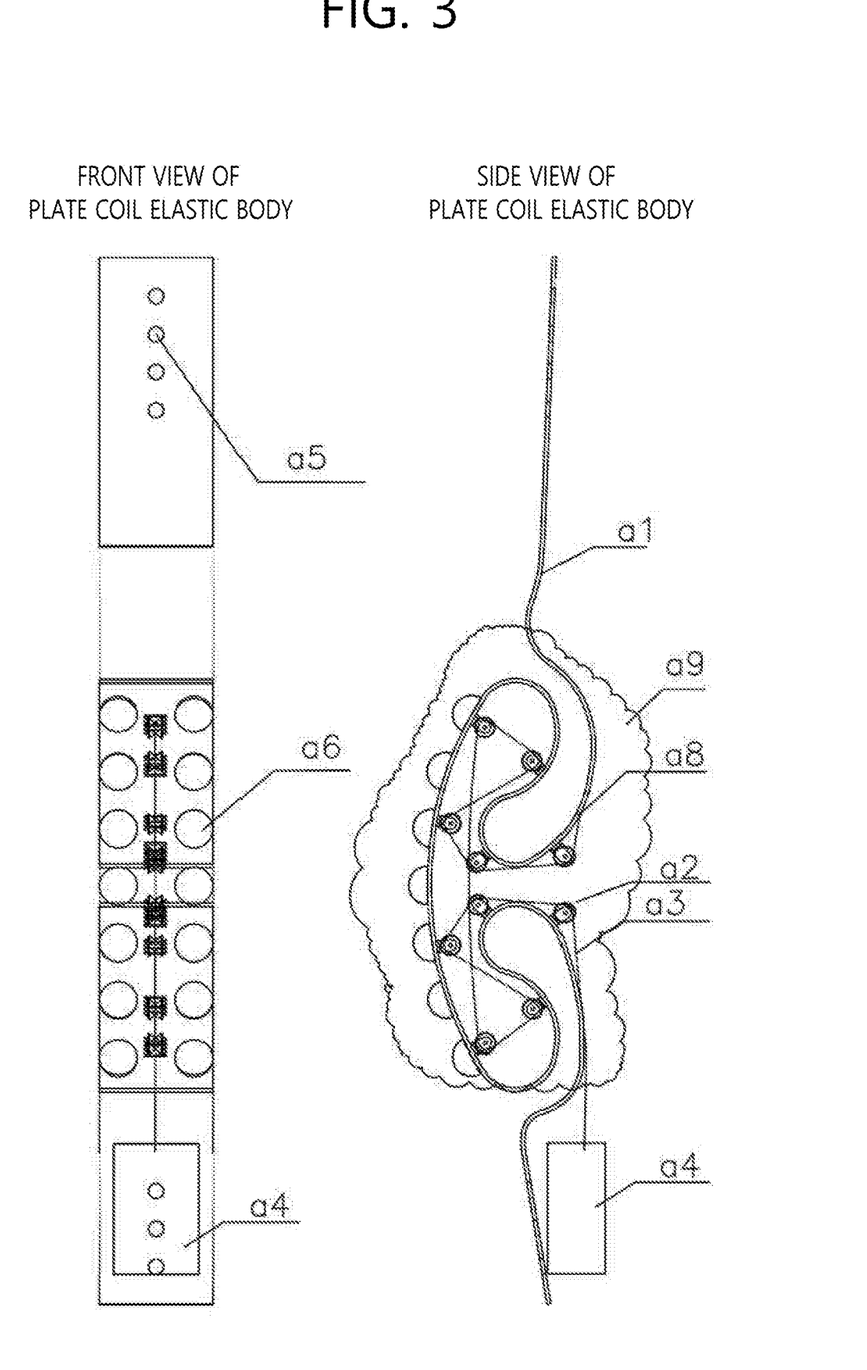
FIG. 3 shows an integrated plate coil elastic body according to the present invention, a device capable of using external power, and acupressure protrusions.

In FIG. 3,

As a plurality of upper and lower frame coupling holes a5 and a7 are provided on the upper side and the lower side of the plate coil elastic body a1, a longitudinal distance may be adjustable according to a height of a user and a change in where the user wears a belt. As a plurality of acupressure protrusions a6 is provided on a surface of a coil part a9 of the plate coil elastic body a1, which comes into contact with a human body, the plate coil elastic body a1 may be prevented from directly pressing the spine when the waist (lumbar) is pressed upon bending of the human body, and the effect of acupressure of muscles on both sides of the spine may be achieved.

A plurality of tension pulleys a2 is installed inside the coil part a9 of the plate coil elastic body a1, and the tension wire a3 having one end fixed to the tension wire fixing point a8 is connected to the tension winch a4 through the tension pulleys a2. If the tension winch a4 is operated with external power, the tension wire a3 is pulled with a value that is set to the tension winch a4, and this pulling force is combined with a repulsive force of the plate coil elastic body a1, thereby increasing a force of raising an upper body part when the human body is stretched.

Figure 4:
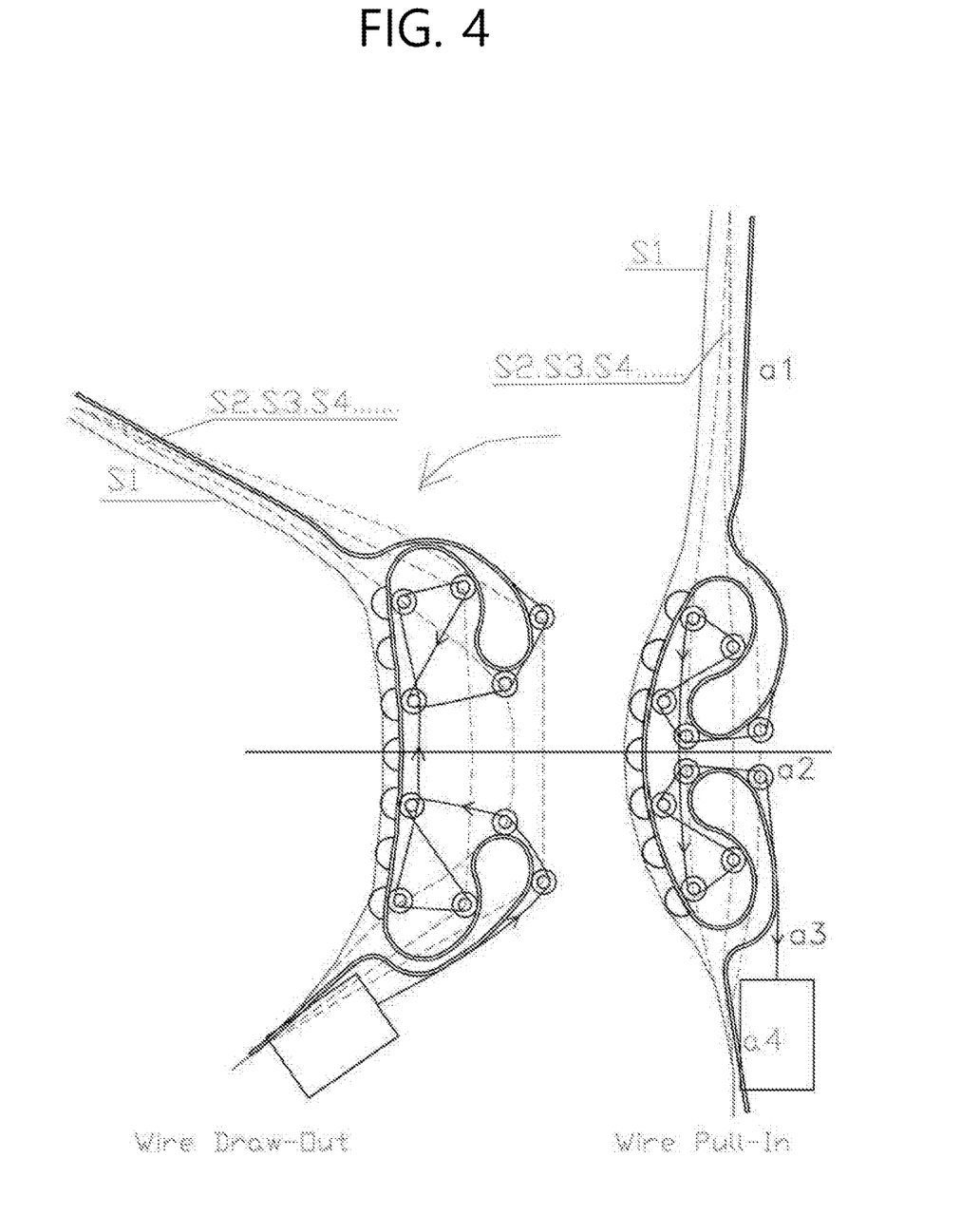
FIG. 4 shows an operation and a principle of an integrated plate coil elastic body according to the present invention in response to bending and stretching of a human body.

In FIG. 4,

There are described the principle of how the plate coil elastic body a1 and a tensioning device installed in the plate coil elastic body operates upon bending and stretching of a human body, and effects thereof.

A reference axis S1 formed along a rear surface (back) of a human body changes in shape but does not change in length.

Virtual variable axis S2, S3, S4, . . . of infinite number formed behind the reference axis S1 changes in length proportionally to an angle of bending or stretching, and the circumference of the coil also changes proportionally due to the change in length. When the human body bends in a vertical state, a bending repulsive force of the plate coil elastic body a1 occurs along the reference axis S1, and a tension repulsive force of the coil occurs along the variable axis S2, S3, S4, . . . , which pass through the coil part, due to extension of the length. Due to the cross-sectional distance between the reference axis S1 and the variable axis S2, S3, S4, . . . , the tensing repulsive force of the coil acts as a bending repulsive force along the reference axis S1.

As a result, the change in elasticity of the plate coil elastic body a1 due to bending of the human body is a bending repulsive force along the reference axis S1 and acts on the human body through the upper and lower frames b1 and c1.

Meanwhile, the tensioning device using external power is mounted to the coil part of the plate coil elastic body a1. In this device, when the plate coil elastic body a1 bends from an upright state upon a human motion, a distance between the tension pulleys a2 is increased due to increase in the circumference of the coil, and a distance for the tension wire a3 to be connected to the tension winch a4 through the tension wire fixing point a8 and the tension pulleys a2 is increased. Due to the increased length, the tension winch a4 draws out the wire while maintaining the tension adjusted to low.

If the plate coil elastic body a1 changes from a bent state to a upright state due to a human motion, reduction in the circumference of the coil makes the distance between the tension pulleys a2 and the distance for the tension wire a3 to be connected to the tension winch a4 through the tension wire fixing point a8 and the tension pulleys a2 is reduced. At this point, the tension winch a4 having received an electric (or mechanical) signal upon the human motion holds back or pulls in the wire to a preset position, while maintaining tension set to high. As the wire is drawn out or held back by bending and stretching with external power, a pulling force of the tension winch a4 is added to a repulsive force of the plate coil elastic body a1, thereby helping extend (or raise) the human body with a greater force.

Figure 5:
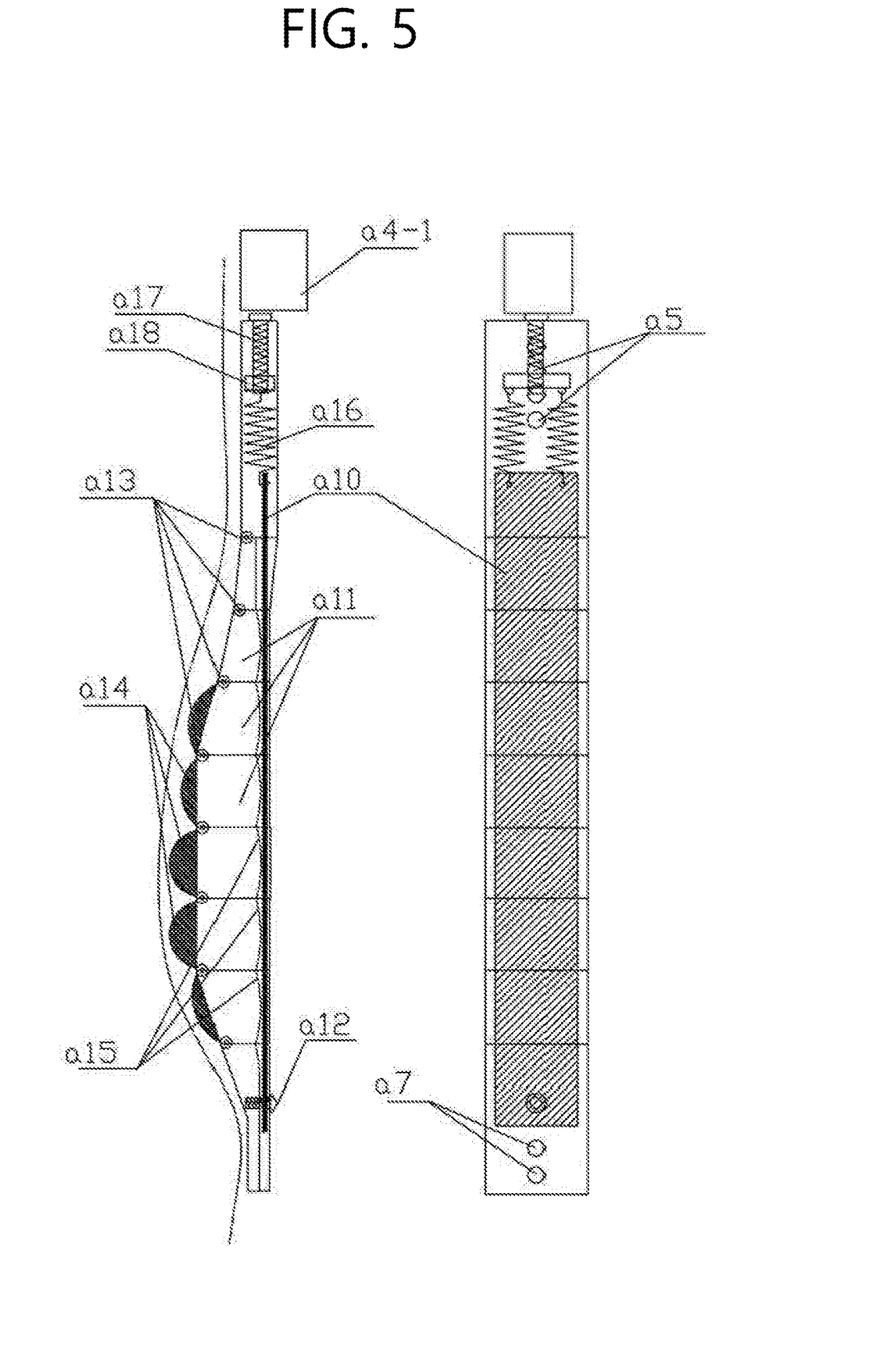
FIG. 5 shows a structure of a block-type complex elastic body, and various shapes and functions of cushions in contact with a curved surface of a back of a human body.

In FIG. 5,

In the complex elastic body a1-1, the plurality of blocks a11 are coupled to hinges or the ball joints a13, and an axis formed by the coupled hinges or ball joints serves as the acting reference axis S1 of the complex elastic body, and this axis does not change in length when the complex elastic body is bent. In the inside of the blocks opposite to connection points of the blocks, the plate spring a10, the coil spring a16, the tension adjustment screw a17, and the tension adjustment nut a18 are connected on the same axis to form the variable axis S2, and, when the complex elastic body a1-1 is bent, this axis increases in length proportionally to an angle of the bending. The increase in length of the variable axis S2 increases tension of the coil spring a16, and this tension acts as a bending repulsive force against the bending of the complex elastic body.

The tension of the coil spring a16 is adjustable by the tension adjustment screw a17, and, the tension adjustment nut a18 moves up and down according to rotation of the tension adjustment screw, pulling or drawing out the coil spring a16 to adjust. At this point, a wall surface of the highest block serves to guide the tension adjustment nut a18. The total bending repulsive force of the complex elastic body a1-1 consists of a repulsive force of the plate spring a10 itself and a repulsive force converted from a tensile force applied to the variable axis S2.

Figure 6:
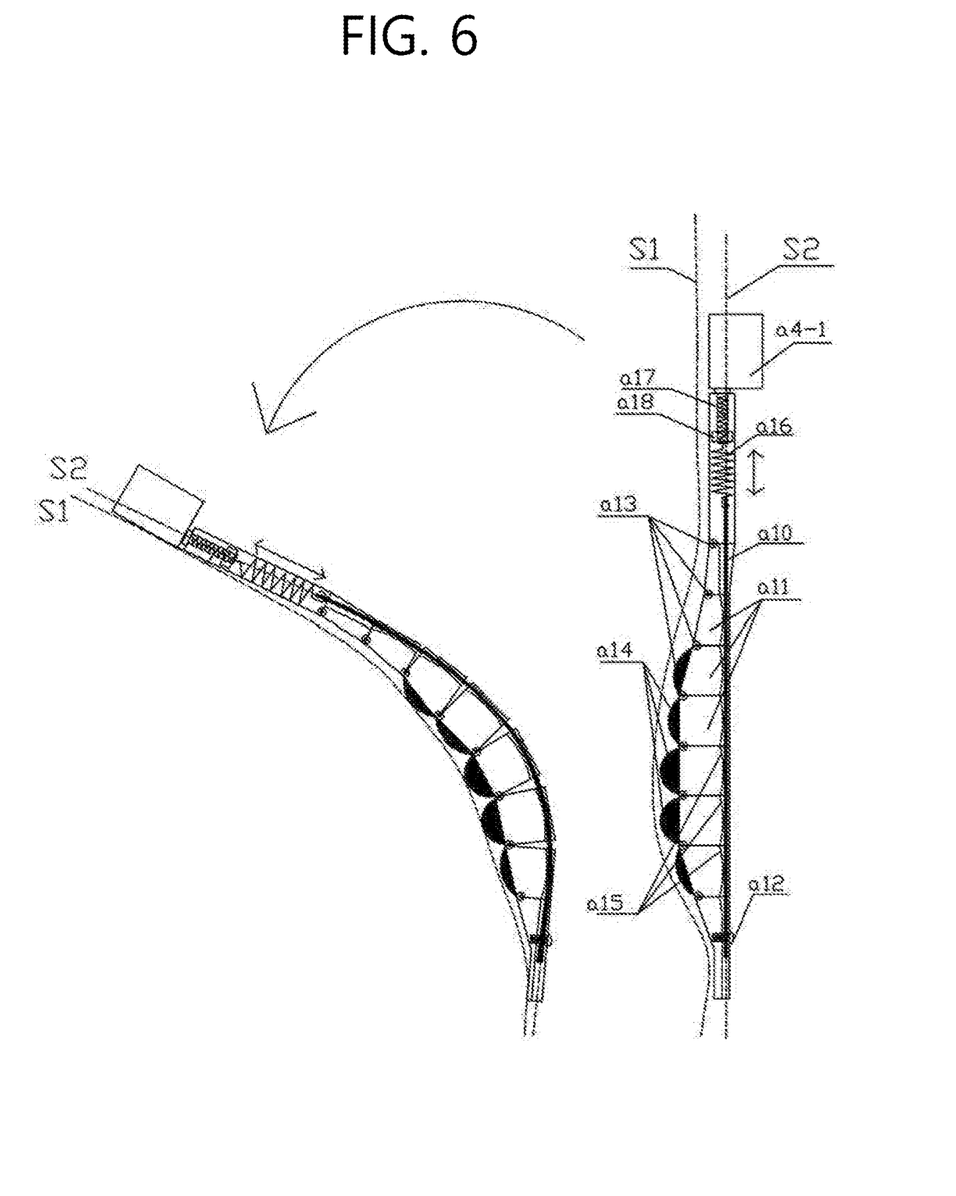
FIG. 6 shows an operation and an operating principle of a complex elastic body according to the present invention in response to bending and stretching of a human body.

In FIG. 6,

The plate spring a10 forming the variable axis S2 penetrates the plurality of blocks a11, and this plate spring forms an arc of the variable axis S2 along a curved sliding guide a15 in a block inner passage when the complex elastic body a1-1 bends, and the plate spring is brought into contact with a surface of the sliding guide a15 upon the bending of the complex elastic body a1-1, thereby slightly moving up and down.

The reference axis S1 does not change in length upon bending, and the varying axis S2 changes in length upon bending, and this change in length occurs due to difference in a circumference by a bending radius of the reference axis S1 and a bending radius of the varying axis S2. The change in length of the variable axis S2 causes the coil spring a16 to be pulled, thereby generating tension, and this tension is converted into a bending reactive elastic force and combined with a bending reactive elastic force of the plate spring a10.

A tension adjustment motor a4-1 is installed in the highest block of the complex elastic body a1-1, and the tension adjustment motor is connected to a coil spring a16 for tension adjustment through the tension adjustment screw a17 and the tension adjustment nut a18. If the tension adjustment motor a4-1 is operated with external power, the plate spring a10 is pulled with a preset value, and this pulling force changes into a bending repulsive force in response to a change in length of the fixed axis S1 and the variable axis S2 due to a block structure, and this repulsive force is combined with a repulsive force of the complex elastic body a1-1, thereby increasing a force of raising an upper body part when the human body is stretched.

In FIGS. 3 to 6,

Cushions a14 having various arc shapes and attached to the blocks a11 of the plate coil elastic body a1, or the acupressure protrusions a6 attached on the coil pat a9 of the complex elastic body a1-1 are positioned around a waist and act as supports upon bending of the plate coil elastic body a1 or the complex elastic body a1-1 to bring about the effect of pressure and acupressure the waist, and the cushions a14 or the acupressure protrusions a6 prevent the lumbar from moving backward even when a user bends his or her back for a long time, thereby helping the back not to be damaged.

INDUSTRIAL APPLICABILITY

The present invention may be applied to a waist part of a wearable robot so as to enhance a bending and stretching capability of a user for a medical purpose.

The invention claimed is:
1. A device for assisting bending and stretching of a human body, the device comprises:
   a plate coil elastic body shaped to conform to curvature of a back of the human body so as to use a bending repulsive force, a rotating repulsive force, and a tension repulsive force;

upper and lower frames worn on upper and lower body parts with wearing belts and having a bending repulsive force;

an extension frame assisting elasticity and fixation of the lower frame; and a tensioning device forcing the plate coil elastic body to return with external power stored in a storage battery, wherein energy required for bending and stretching of the human body is reused using a repulsive force of a spring, which increases proportionally to an angle of the bending of the human body, wherein a return force of the plate coil elastic body is increased with the external power so as to reduce load on the human body or increasing bending and stretching capability of the human body, and wherein the device generates electricity from a force occurring due to a change in position when the human body bends, and charges the storage battery so as to increase a time to be driven by electric power from the storage battery.

2. The device of claim 1, wherein, when a coil part of the plate coil elastic body acts as a support upon the bending of the human body to thereby press the back forward, acupressure protrusions press both sides of spine and functioning as a cushion between the elastic body and the spine.

3. The device of claim 1, wherein a used principle is that the elastic body bends by a cross-sectional distance between a length fixed axis (s1) with reference to a curved surface of the back of the human body and a variable axis (s2, s3, s4,...) of infinite number, which is present between the back of the human body and the elastic body, and that virtual points on the fixed axis (s1) acts as support positions upon the bending of the human body.

4. The device of claim 1, wherein a plurality of points, whose positions change significantly when a shape of the plate coil elastic body changes upon the bending and stretching of the human body, are selected and a distance between the plurality of points is forcibly controlled with the external power, so that an additional external force is applied when the plate coil elastic body returns (to be stretched from a bending state), thereby enhancing performance.

5. A device for assisting bending and stretching of a human body, the device comprising:

a block frame formed of a plurality of blocks in different shapes and sizes so as to form a frame arbitrarily adjustable to conform to a back of the human body in various shapes, wherein a plate spring, a buffer spring, a tension adjustment bolt, and an tension adjustment motor are connected on one axis through an inner sliding passage formed in the block frame so that a bending repulsive force of the plate spring and a rotational force of the tension adjustment motor act as a total repulsive force of the frame;

upper and lower frames to be worn on upper and lower body parts; and an extension frame for assisting elasticity and fixation of the lower frame, wherein a bending and stretching capability of the human body is enhanced and load on the body is reduced with the repulsive force of the block frame increasing proportionally to a bending angle of the human body, wherein backward displacement of spine is restrained directly by pressure of the blocks when the upper body bends, and wherein the device generates electricity from a force occurring due to a change in position when the human body bends, and charges a storage battery so as to increase a time to be driven by electric power from the storage battery.

6. The device of claim 5, wherein there are formed a length fixed axis (S1) with reference to a surface of the block frame in contact with the human body, and a length variable axis (S2) with reference to the inner sliding passage in the block frame, and an bending and stretching angle of the block frame and a bending and stretching force of the block frame are controllable by controlling a length of the variable axis (S2).

* * * * *